US012747427B2

(12) United States Patent
Lee et al.

(10) Patent No.: US 12,747,427 B2
(45) Date of Patent: Sep. 29, 2026

(54) METHOD FOR PRODUCTION OF VARICELLA ZOSTER VIRUS SURFACE PROTEIN ANTIGEN

(71) Applicant: GREEN CROSS CORPORATION, Yongin-si (KR)

(72) Inventors: Kwang Bae Lee, Yongin-si (KR); Mi Suk Kim, Yongin-si (KR); Jung Ae Lim, Yongin-si (KR); Yoo Min Jeong, Yongin-si (KR); Seung Ryel Han, Yongin-si (KR); Ji Yeon Kim, Yongin-si (KR); Ji Sung You, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 862 days.

(21) Appl. No.: 18/014,296

(22) PCT Filed: Jul. 6, 2021

(86) PCT No.: PCT/KR2021/008537
§ 371 (c)(1),
(2) Date: Jan. 3, 2023

(87) PCT Pub. No.: WO2022/010213
PCT Pub. Date: Jan. 13, 2022

(65) Prior Publication Data

US 2023/0257718 A1 Aug. 17, 2023

(30) Foreign Application Priority Data

Jul. 10, 2020 (KR) ........................ 10-2020-0085685

(51) Int. Cl.
*C07K 14/47* (2006.01)
*C07K 14/005* (2006.01)
(Continued)

(52) U.S. Cl.
CPC .............. *C12N 7/00* (2013.01); *C07K 14/005* (2013.01); *C12N 2710/16751* (2013.01); *C12N 2710/16763* (2013.01)

(58) Field of Classification Search
CPC ........ C07K 14/005; C12N 2710/16751; C12N 2710/16763; C12N 2710/16034;
(Continued)

(56) References Cited

U.S. PATENT DOCUMENTS 5,653,976 A 8/1997 Shiraki et al.
7,939,084 B1 5/2011 Hanon et al.
(Continued)

FOREIGN PATENT DOCUMENTS

CN 105175548 A 12/2015
CN 108992667 A 12/2018
(Continued)

OTHER PUBLICATIONS

Warreth, S. (Dec. 17, 2019). Viral clearance studies for the biopharmaceutical industry. BioProcess International. https://www.bioprocessintl.com/viral-clearance/detection-and-clearance-of-viruses-in-the-biopharmaceutical-industry (Year: 2019).*
(Continued)

*Primary Examiner* — Robert B Mondesi
(74) *Attorney, Agent, or Firm* — Sughrue Mion, PLLC

(57) ABSTRACT

A method for production of a Varicella Zoster Virus surface protein antigen is disclosed. The method for production of a Varicella Zoster Virus surface protein antigen is an effective production method capable of obtaining the Varicella Zoster Virus surface protein antigen in high yield and high purity. Therefore, the method is useful for production of the Varicella Zoster Virus surface protein antigen for use as a
(Continued)

vaccine composition for preventing or treating varicella or herpes zoster.

15 Claims, 8 Drawing Sheets

Specification includes a Sequence Listing.

(51) Int. Cl.
*C12N 7/00* (2006.01)
*C12N 15/86* (2006.01)

(58) Field of Classification Search
CPC .......... C12N 2710/16151; C12N 2710/16734; C12N 2710/16051; C12N 2710/16064; A61K 39/12
USPC ........................................................ 435/69.3
See application file for complete search history.

(56) References Cited

U.S. PATENT DOCUMENTS

| | | | | |
|---|---|---|---|---|
| 2016/0304902 | A1 | 10/2016 | Kim et al. | |
| 2019/0365884 | A1* | 12/2019 | Nam | A61P 31/20 |
| 2021/0187099 | A1* | 6/2021 | Nam | A61P 31/22 |

FOREIGN PATENT DOCUMENTS

| | | | |
|---|---|---|---|
| JP | 2002-518011 | A | 6/2002 |
| JP | 2017-501974 | A | 1/2017 |
| JP | 2018-510867 | A | 4/2018 |
| KR | 10-1995-0701970 | A | 5/1995 |
| KR | 10-2007-0110413 | A | 11/2007 |
| KR | 10-1591823 | B1 | 1/2016 |
| KR | 10-2018-0059371 | A | 6/2018 |
| KR | 10-2019-0099269 | A | 8/2019 |
| WO | 99/66044 | A1 | 12/1999 |
| WO | 2006/094756 | A2 | 9/2006 |
| WO | 2015/073633 | A1 | 5/2015 |
| WO | 2016/149088 | A1 | 9/2016 |
| WO | 2019/225962 | A1 | 11/2019 |

OTHER PUBLICATIONS

Bio-Rad, Ng, P. (2006). Chromatography—how CHTTM ceramic hydroxyapatite . . . https://www.bio-rad.com/webroot/web/pdf/lsr/literature/Bulletin_5518.pdf (Year: 2006).*

Elisabeth Thomsson et al., "Recombinant glycoprotein E produced in mammalian cells in large-scale as an antigen for vericella-zoster-virus serology", Journal of Virological Methods, 2011, Vo. 175, pp. 53-59 (7 pages total).

Adriana Weinberg, et al., "Varicella-Zoster Virus-Specific Immune Responses to Herpes Zoster in Elderly Participants in a Trial of a Clinically Effective Zoster Vaccine", The Journal of Infectious Diseases, Oct. 1, 2022, pp. 1068 to 1077, vol. 2009, No. 200.

Charlotte Warren-Gash, et al., "Varicella and herpes zoster vaccine development: lessons learned", Expert Review of Vaccines, 2017, pp. 1191-1201, vol. 16, No. 12.

Kazuaki Furukawa, et al., "Enhancement of productivity of recombinant α-amidating enzyme by low temperature culture", Cytotechnology, 1999, pp. 85-94, vol. 31.

Sung Kwan Yoon, et al., "Enhancing Effect of Low Culture Temperature on Specific Antibody Productivity of Recombinant Chinese Hamster Ovary Cells: Clonal Variation", Biotechnol. Prog., 2004, 1683-1688, vol. 20, No. 6.

International Search Report for PCT/KR2021/008537 dated Oct. 12, 2021 [PCT/ISA/210].

Kelly Zhang et al., "Mixed-mode chromatography in pharmaceutical and biopharmaceutical applications", Journal of Pharmaceutical and Biomedical Analysis, vol. 128, 2016, pp. 73-88.

Communication dated Jul. 8, 2026, in Indian Application No. 202317001966.

* cited by examiner

[Fig. 1]
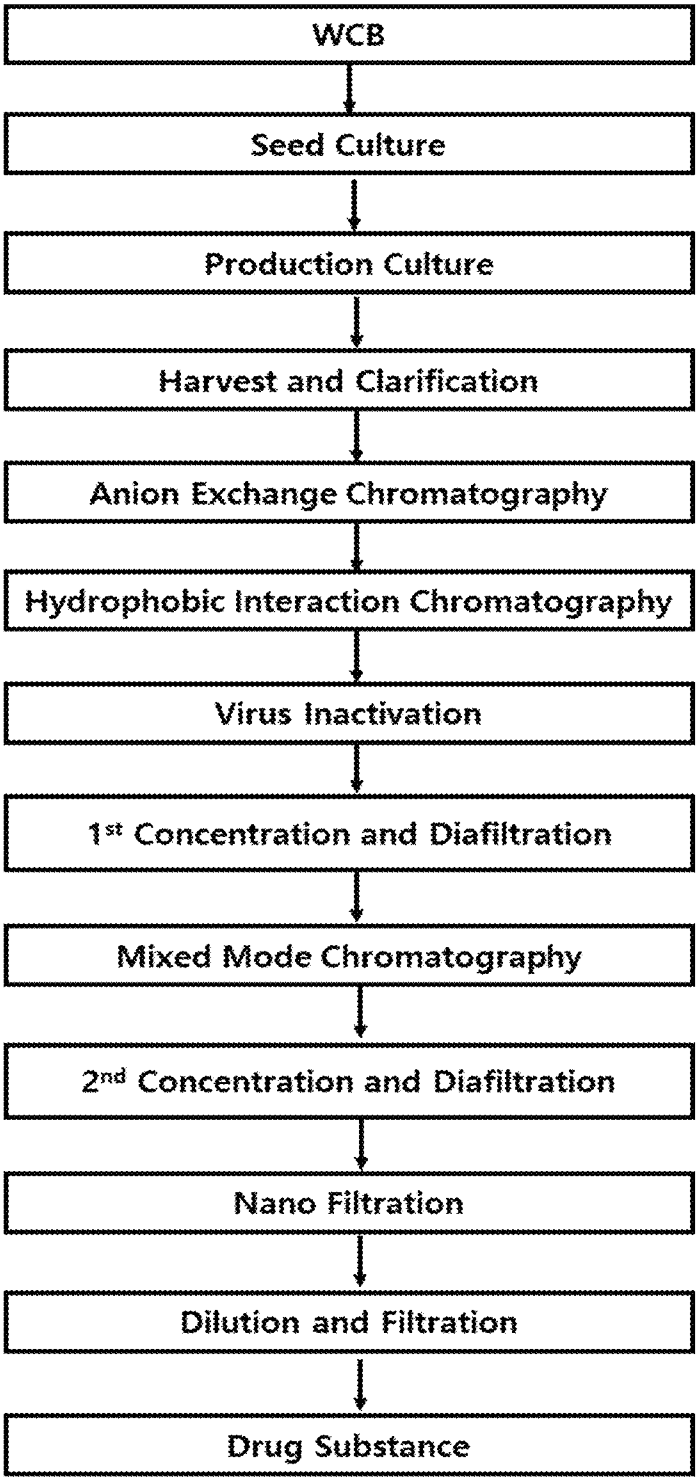

[Fig. 2]
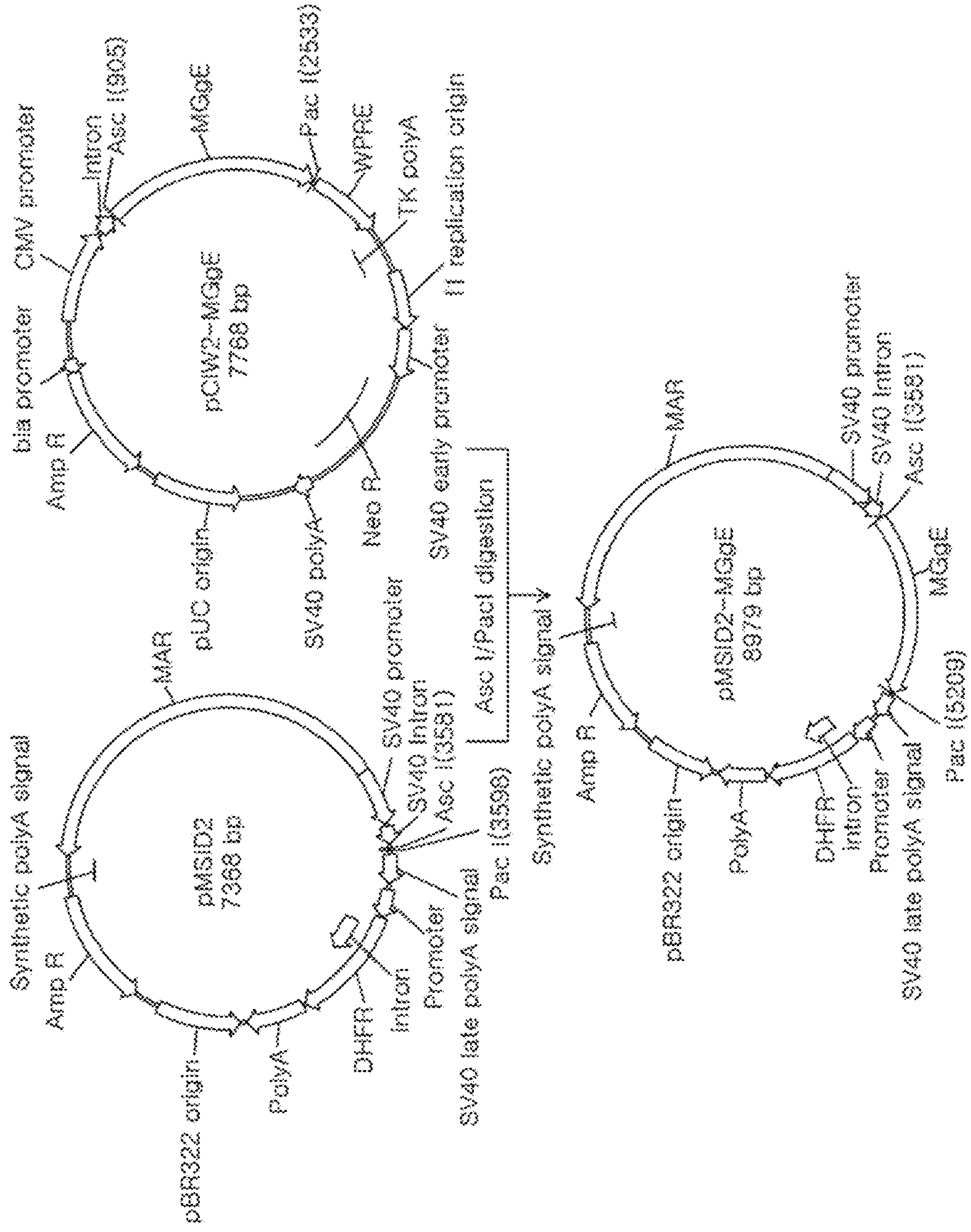

[Fig. 3]
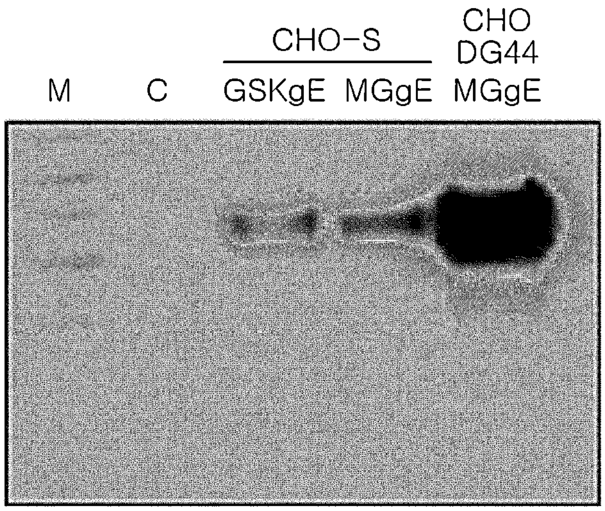
C : CHO-S
GSKgE-CHO-S : MTX 50nM / 6day
MGgE-CHO-S : MTX 50nM / 6day
MGgE-CHO-DG44 : MTX 20nM / 6day

[Fig. 4]
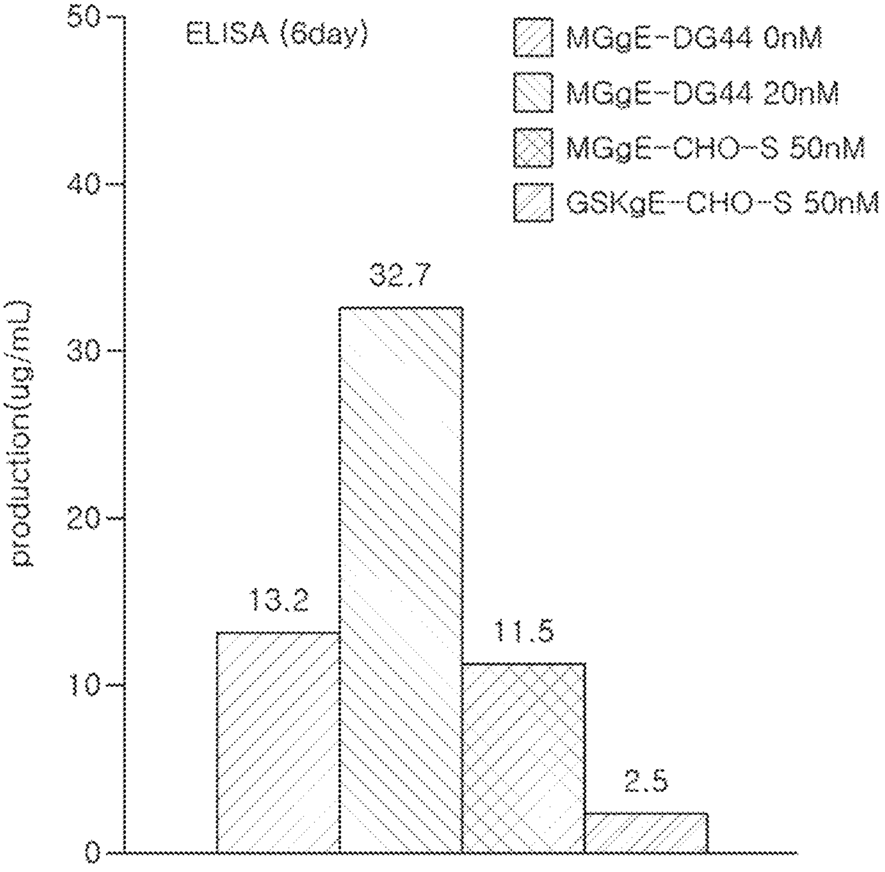

[Fig. 5a]
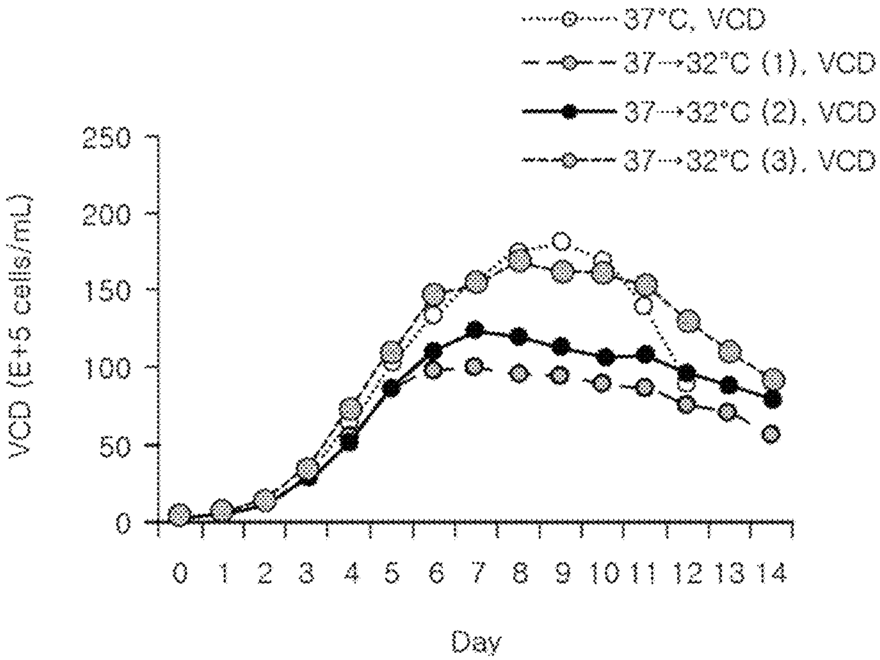

[Fig. 5b]
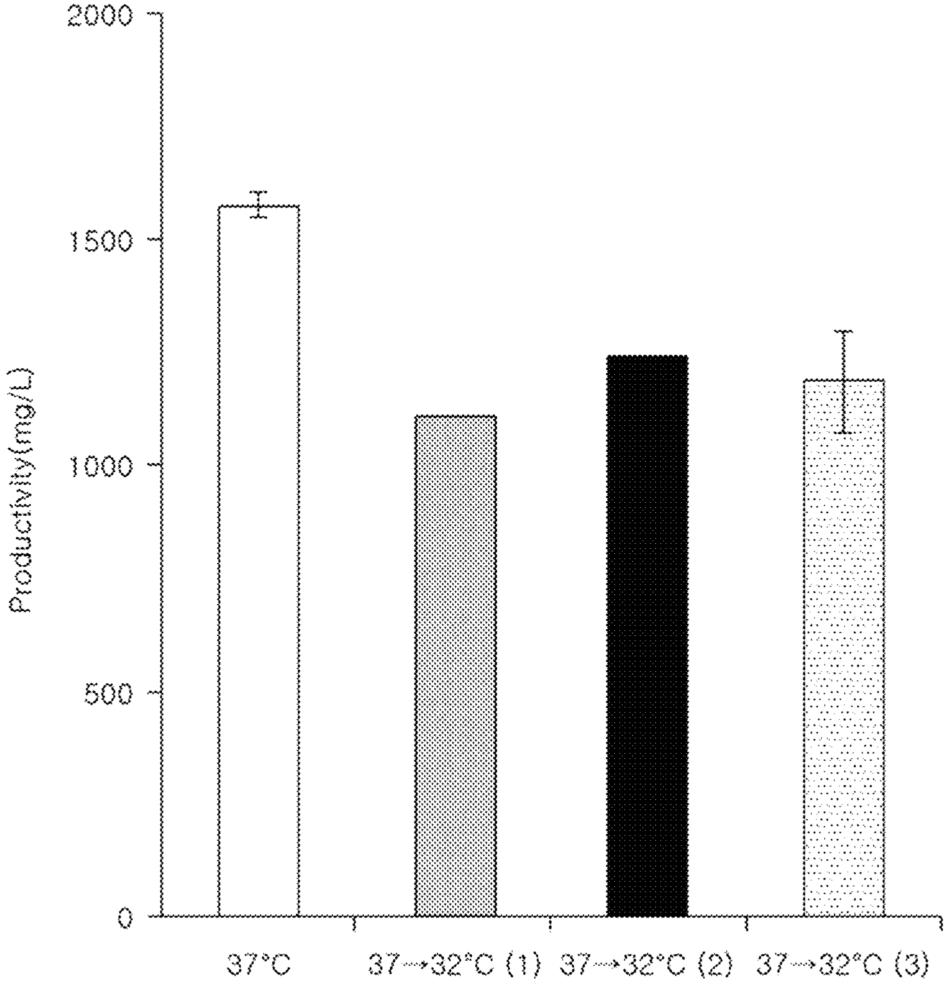

[Fig. 6a]
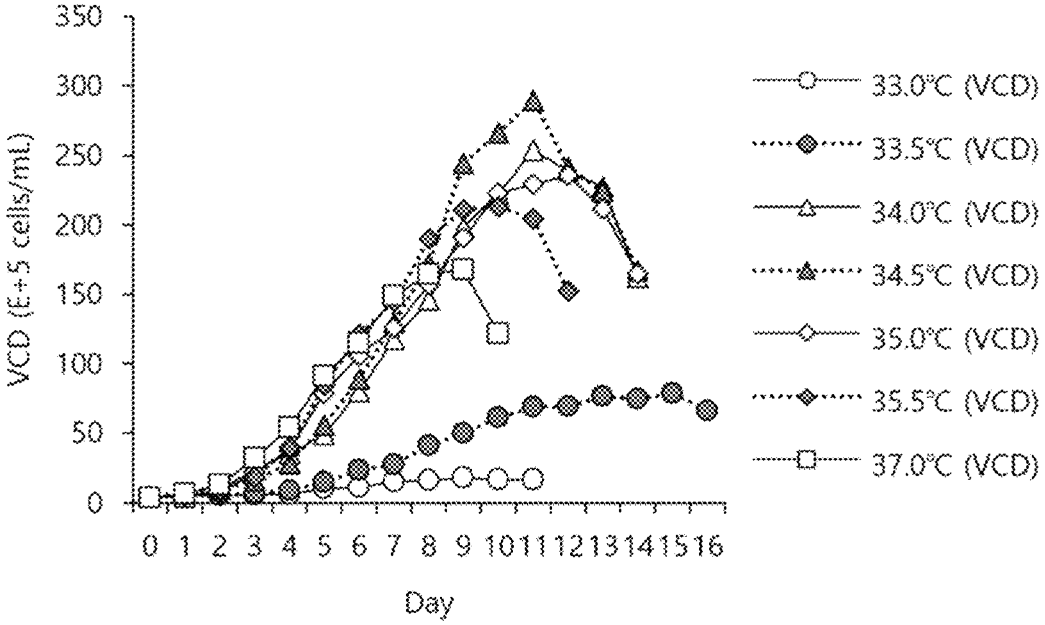

[Fig. 6b]
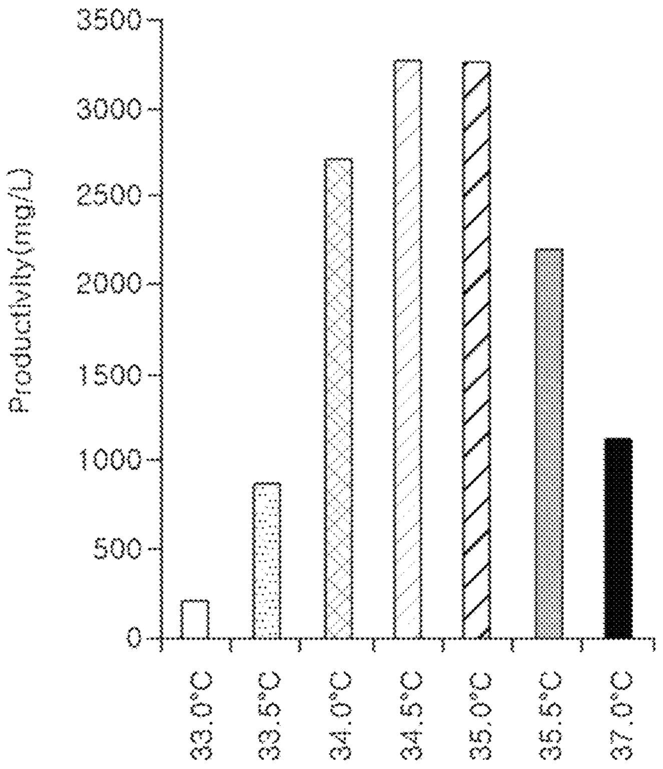

SEQUENCE LISTING

<160> NUMBER OF SEQ ID NOS: 4

<210> SEQ ID NO 1
<211> LENGTH: 537
<212> TYPE: PRT
<213> ORGANISM: Artificial Sequence
<220> FEATURE:
<223> OTHER INFORMATION: MGgE antigen

<400> SEQUENCE: 1

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Thr Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

Glu Leu Glu Leu Asp Pro Pro Glu Ile Glu Pro Gly Val Leu Lys Val
275 280 285

Leu Arg Thr Glu Lys Gln Tyr Leu Gly Val Tyr Ile Trp Asn Met Arg
290 295 300

Gly Ser Asp Gly Thr Ser Thr Tyr Ala Thr Phe Leu Val Thr Trp Lys
305 310 315 320

Gly Asp Glu Lys Thr Arg Asn Pro Thr Pro Ala Val Thr Pro Gln Pro
325 330 335

Arg Gly Ala Glu Phe His Met Trp Asn Tyr His Ser His Val Phe Ser
340 345 350

Val Gly Asp Thr Phe Ser Leu Ala Met His Leu Gln Tyr Lys Ile His

```
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg
    530                 535


<210> SEQ ID NO 2
<211> LENGTH: 1610
<212> TYPE: DNA
<213> ORGANISM: Artificial Sequence
<220> FEATURE:
<223> OTHER INFORMATION: MGgE antigen

<400> SEQUENCE: 2

atgggaacag tcaacaaacc agtcgtcggc gtgctgatgg gcttcggtat tattacagga     60

actctgagga ttactaaccc cgtgcgcgcc tctgtgctgc ggtacgacga tttccacaca    120

gacgaggata agctggacac caattccgtg tatgagccct actatcactc tgatcacgcc    180

gagagctcct gggtgaaccg gggcgagtct agcaggaagg cttacgacca caacagccct    240

tatatctggc cacggaatga ctacgatggc tttctggaga acgcccacga gcaccacggc    300

gtgtataatc agggcagagg catcgactct ggcgagcggc tgatgcagcc cacccagatg    360

agcgcccagg aggatctggg cgacgataca ggcatccacg tgatccctac cctgaatggc    420

gacgataggc acaagatcgt gaacgtggat cagagacagt acggcgacgt gttcaagggc    480

gatctgaatc ccaagcctca gggccagagg ctgatcgagg tgtccgtgga ggagaaccac    540

cccttcaccc tgagagcccc tatccagcgg atctacggcg tgaggtatac cgagacatgg    600

agctttctgc catccctgac atgcaccggc gacgctgctc ctgctatcca gcacatctgc    660

ctgaagcaca ccacatgttt tcaggacgtg gtggtggacg tggattgtgc cgagaataca    720

aaggaggatc agctggctga gatctcctac cggttccagg gcaagaagga ggccgatcag    780

ccttggatcg tggtgaacac ctctacactg tttgacgagc tggagctgga tccccctgag    840

atcgagccag gcgtgctgaa ggtgctgaga accgagaagc agtacctggg cgtgtatatc    900

tggaacatgc ggggctctga cggcaccagc acatacgcta ccttcctggt cacatggaag    960

ggcgatgaga agacccggaa tccaacacct gctgtgaccc ctcagccaag gggagctgag   1020
```

```
tttcacatgt ggaactatca ctcccacgtg ttctctgtgg gcgacacctt tagcctggcc   1080

atgcacctgc aatataagat ccacgaggct cctttcgacc tgctgctgga gtggctgtat   1140

gtgcccatcg atcctacatg ccagccaatg aggctgtact ccacctgtct gtatcaccca   1200

aatgcccccc aatgcctgag ccacatgaac tccggctgta cctttacaag cccccacctg   1260

gcccagagag tggcttccac agtgtaccag aactgcgagc acgccgacaa ttacaccgct   1320

tattgtctgg gcatctctca catggagccc agcttcggcc tgatcctgca cgacggcggc   1380

accacactga agtttgtgga tacacccgag tccctgtctg gcctctacgt gttcgtggtg   1440

tacttcaacg gccacgtgga ggccgtggct tatacagtgg tgtctaccgt ggatcacttc   1500

gtgaacgcca tcgaggagag aggatttcca cctaccgctg gacagcctcc agctaccaca   1560

aagcctaagg aaatcacccc tgtcaatcct ggaacttcac ctctgctgcg              1610


<210> SEQ ID NO 3
<211> LENGTH: 623
<212> TYPE: PRT
<213> ORGANISM: Artificial Sequence
<220> FEATURE:
<223> OTHER INFORMATION: VZV gE antigen

<400> SEQUENCE: 3

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
```

```
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620


<210> SEQ ID NO 4
<211> LENGTH: 546
<212> TYPE: PRT
<213> ORGANISM: Artificial Sequence
<220> FEATURE:
<223> OTHER INFORMATION: GSKgE

<400> SEQUENCE: 4

Met Gly Thr Val Asn Lys Pro Val Val Gly Val Leu Met Gly Phe Gly
```

-continued

```
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430
```

-continued

```
Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala
545
```

METHOD FOR PRODUCTION OF VARICELLA ZOSTER VIRUS SURFACE PROTEIN ANTIGEN

CROSS REFERENCE TO RELATED APPLICATIONS

This application is a National Stage of International Application No. PCT/KR2021/008537 filed Jul. 6, 2021, claiming priority based on Korean Patent Application No. 10-2020-0085685 filed Jul. 10, 2020.

INCORPORATION BY REFERENCE OF SEQUENCE LISTING

The content of the electronically submitted sequence listing, file name: Q282769_Sequence_Listing_As_Filed.txt; size: 16,224 bytes; and date of creation: Dec. 2, 2022, filed herewith, is incorporated herein by reference in its entirety.

TECHNICAL FIELD

The present invention relates to a method for producing Varicella Zoster Virus surface protein antigens.

BACKGROUND ART

Varicella Zoster Virus (VZV) is a virus that causes varicella mainly in children and adolescents. Once infection occurs, VZV remains dormant in sensory root and cranial nerve ganglion cells for several years, and is reactivated and causes herpes zoster in adulthood when immunity decreases. Varicella is highly contagious; and once infection occurs, it causes a blister-like rash all over the body with fever and malaise. In most normal children, varicella rarely progresses to a serious condition and eventually progresses to a self-limited disease. However, it is known that many cases where varicella progresses to serious symptoms occur in patients who have undergone organ transplantation or chemotherapy (Adriana Weinberg et al., J Infectious Diseases, 200(7): 1068, 2009; Judith Breuer et al., Expert Review of Vaccines, 2017, DOI:10.1080/14760584.2017.1394843).

Herpes zoster has initial symptoms of aches and pains all over the body like body aches, or sensations of severe itching, tingling, and burning, with severe pain like being stabbed with a knife. Herpes zoster is a disease in which blisters develop after a few days, pain increases as skin lesions increase, and older patients tend to complain of more severe pain. Even in a case where herpes zoster is cured, it may leave neuralgia as a sequela. It is known that in people aged 60 or higher, the neuralgia may cause them to sleep fitfully, cause them to complain of chronic fatigue, cause them to feel severe pain even upon light contact or friction, or cause even depression, although such neuralgia is relatively rare in adults aged 40 or lower.

ZOSTAVAX (Merck & Co, Inc.), which is a live attenuated vaccine produced using Oka strain, was developed as a preventive vaccine against herpes zoster. This vaccine has been approved and sold in the US and Korea under a condition that it should be used for adults aged 50 or higher, not for children or adolescents, due to the fact that a large amount of virus is contained in the vaccine. Recently, a vaccine composed of a viral surface protein (gE) and an adjuvant, which is intended for adults aged 50 or higher, was developed by GlaxoSmithKline Biologicals SA, and proved to have preventive efficacy in clinical trials (U.S. Pat. No. 7,939,084).

DISCLOSURE OF INVENTION

Technical Problem

Accordingly, while having conducted studies on a method capable of increasing productivity of Varicella Zoster Virus (VZV) surface protein (gE) antigens without affecting immunogenicity thereof, the present inventors have found a culture and purification method capable of improving productivity of the VZV gE antigens, and thus have completed the present invention.

Solution to Problem

In an aspect of the present invention, there is provided a method for producing Varicella Zoster Virus (VZV) surface protein (gE) antigens, comprising steps of: (a) culturing a recombinant cell line that produces the VZV gE antigens, to obtain a culture solution; and (b) purifying the culture solution.

The culture solution obtaining step (a) may comprise steps of: (a-1) performing seed culture on the recombinant cell line; and (a-2) performing production culture on the cell line that has undergone the seed culture.

The culture solution purifying step (b) may comprise steps of: performing anion exchange chromatography; performing hydrophobic interaction chromatography; subjecting the culture solution to treatment with a virus-inactivating agent, to inactivate viruses; performing mixed-mode chromatography; and performing concentration and filtration.

Advantageous Effects of Invention

The method for producing Varicella Zoster Virus surface protein antigens according to the present invention is an effective production method capable of obtaining the Varicella Zoster Virus surface protein antigens in high yield and high purity. Therefore, the method is useful for producing Varicella Zoster Virus surface protein antigens for use as a vaccine composition for preventing or treating varicella or herpes zoster.

BRIEF DESCRIPTION OF DRAWINGS

FIG. 1 illustrates a flowchart, showing a process of performing culture and purification for production of VZV gE antigens, according to an embodiment of the present invention.

FIG. 2 illustrates a schematic diagram, showing a process of producing the pMSID2-MGgE vector.

FIG. 3 illustrates a result obtained by identifying, through Western blotting, the productivity of VZV gE depending on types of VZV gE and cell line.

FIG. 4 illustrates a result obtained by identifying, through ELISA, the productivity of VZV gE depending on types of VZV gE and cell line.

FIG. 5A illustrates a result obtained by identifying the viable cell density (VCD) depending on culture temperature shift in a production culture step for the MGgE-introduced cell line.

FIG. 5B illustrates a result obtained by identifying the productivity depending on culture temperature shift in a production culture step for the MGgE-introduced cell line.

FIG. 6A illustrates a result obtained by identifying the viable cell density depending on culture temperatures in a production culture step for the MGgE-introduced cell line.

FIG. 6B illustrates a result obtained by identifying the productivity depending on culture temperatures in a production culture step for the MGgE-introduced cell line.

BEST MODE FOR CARRYING OUT THE INVENTION

Hereinafter, the present invention will be described in detail.

In an aspect of the present invention, there is provided a method for producing Varicella Zoster Virus (VZV) surface protein (gE) antigens, comprising steps of: (a) culturing a recombinant cell line that produces the VZV gE antigens, to obtain a culture solution; and (b) purifying the culture solution.

In the present invention, the Varicella Zoster Virus surface protein antigen may preferably be one of the Varicella Zoster Virus surface protein antigens disclosed in International Publication No. WO 2019/225962 A1. Specifically, the Varicella Zoster Virus surface protein antigen (MGgE) may be a polypeptide consisting of the amino acid sequence represented by SEQ ID NO: 1, and the polypeptide may be encoded by a gene consisting of the nucleotide sequence represented by SEQ ID NO: 2.

The Varicella Zoster Virus surface protein antigen represented by the amino acid sequence of SEQ ID NO: 1 is a Varicella Zoster Virus surface protein antigen variant which is derived from the Varicella Zoster Virus surface protein antigen represented by the amino acid sequence of SEQ ID NO: 3, wherein the antigen variant includes a variation which is truncation of the carboxy terminus of the $537^{th}$ amino acid residue in the Varicella Zoster Virus surface protein antigen.

The variation which is truncation of the carboxy terminus of the $537^{th}$ amino acid residue means that in the direction from amino terminus (N-terminus) to carboxy terminus (C-terminus), $1^{st}$ to $537^{th}$ amino acid residues remain and contiguous amino acid residues from the $538^{th}$ amino acid residue to the carboxy terminus are truncated.

The cell line that produces the VZV gE antigens may be one transformed with a VZV gE antigen-encoding gene that consists of the nucleotide sequence represented by SEQ ID NO: 2. The cell line may have an expression vector containing the VZV gE antigen-encoding gene. In an embodiment of the present invention, the expression vector may be an expression vector including the pMSID2 vector disclosed in Korean Patent No. 1591823. However, for the expression vector, any vector may be used without limitation as long as it is suitable for transfection of the VZV gE antigen into a cell line.

As used herein, the term "vector" refers to a nucleic acid means including a nucleotide sequence that can be introduced into a host cell to be recombined and inserted into the genome of the host cell, or can be spontaneously replicated as an episome. Suitable expression vectors include expression regulatory elements, such as promoters, start codons, stop codons, polyadenylation signals, and enhancers, as well as signal sequences or leader sequences for membrane targeting or secretion, and may be produced variously according to their purpose. The start codon and stop codon must act in an individual when a gene construct encoding a target protein is administered thereto, and must be in-frame with the coding sequence.

The host cell or non-human host subject transfected or transformed with a vector according to an embodiment of the present invention may be a host cell or non-human host subject which is genetically modified with the vector. As used herein, the term "genetically modified" means that a host cell, a non-human host subject, a predecessor, or a parent includes, in addition to its own genome, a polynucleotide or vector according to an embodiment of the present invention which has been into the host cell, the non-human host subject, the predecessor, or the parent. In addition, the polynucleotide or vector according to an embodiment of the present invention may exist in the genetically modified host cell or non-human host subject as an independent molecule, specifically as a replicable molecule, outside the genome thereof or may be stably inserted into the genome of the host cell or non-human host subject.

The host cell according to an embodiment of the present invention is a eukaryotic cell. The eukaryotic cell includes a fungal cell, a plant cell, or an animal cell. Examples of the fungal cell may include yeast, specifically, yeast of *Saccharomyces* sp., and more specifically, *Saccharomyces cerevisiae*. In addition, examples of the animal cell include insect cells or mammalian cells, and specific examples of the animal cell include HEK293, 293T, NSO, CHO, MDCK, U2-OSHela, NIH3T3, MOLT-4, Jurkat, PC-12, PC-3, IMR, NT2N, Sk-n-sh, CaSki, C33A, and the like. In addition, suitable cell lines well known in the art may be obtained from cell line depositories such as American Type Culture Collection (ATCC).

The VZV gE antigen according to the present invention may be expressed in various types of organisms such as bacteria, yeast, mammalian cells, plants, and transgenic animals. Preferably, mammalian cells may be used in view of the regulations on protein therapeutic agents and the fact that the produced protein needs to be similar to its native form. Examples of the mammalian cell include immortal hybridoma cells, NS/O myeloma cells, 293 cells, Chinese hamster ovary cells (CHO cells), HeLa cells, CapT cells (human amniotic fluid-derived cells), COS cells, and the like. According to an embodiment of the present invention, CHO DG44 cells may be used as the mammalian cell.

To introduce the expression vector according to the present invention into the above-mentioned cell line, techniques known in the art may be used, examples of which include electroporation, protoplast fusion, calcium phosphate ($CaPO_4$) precipitation, and calcium chloride ($CaCl_2$) precipitation.

Specifically, the culture solution obtaining step (a) may comprise steps of: (a-1) performing seed culture on the recombinant cell line; and (a-2) performing production culture on the cell line that has undergone the seed culture.

As used herein, the term "seed culture" refers to culture intended for obtaining a cell line in a large amount. The seed culture may be performed at a temperature condition that allows the number of cells to increase most actively. In other words, the seed culture may be performed so that a certain number of cells are obtained for a cell line.

As used herein, the term "production culture" refers to mass culture of a cell line which is intended for producing a recombinant protein.

The seed culture performing step (a-1) may be such that the VZV gE antigen-producing cell line is cultured by any one method selected from the group consisting of subculture, suspension culture, and combinations thereof. For example, seed culture of the VZV gE antigen-producing cell line may be performed by subculture and suspension culture, and production culture thereof may be performed by suspension culture.

As used herein, the term “subculture” refers to a method of culturing a cell line while transferring the cell line to the same or different fresh medium depending on a culture cycle.

In an embodiment of the present invention, the subculture may be carried out by transferring and inoculating the cell line to the same fresh medium at intervals of 1 to 7 days, 2 to 5 days, or 3 to 4 days. Here, the number of cells inoculated may be, but is not limited to, $2\times10^5$ cells/mL to $5\times10^5$ cells/mL, $3\times10^5$ cells/mL to $4\times10^5$ cells/mL, or $4\times10^5$ cells/mL. In addition, the $CO_2$ concentration in the subculture may be, but is not limited to, 4.0% to 6.0%, 4.5% to 5.5%, or 5.0%.

As used herein, the term “suspension culture” refers to a culture method in which cells are suspended in a culture solution. It is possible to carry out suspension culture on cells that proliferate in a suspended state even in vivo, such as blood cells or cancer cells in ascites, without shaking or rotation; however, in most cases, suspension culture may be carried out by rotating a stirring blade (agitation culture), shaking each culture bottle (shaking culture), or rotating an incubator (rotary culture).

In an embodiment of the present invention, the suspension culture may be carried out at a stirring speed condition of 86 rpm to 96 rpm, 88 rpm to 94 rpm, or 90 rpm to 92 rpm; however, the stirring speed is not limited thereto. The number of cells inoculated in the suspension culture may be, but is not limited to, $2\times10^5$ cells/mL to $5\times10^5$ cells/mL, $3\times10^5$ cells/mL to $4\times10^5$ cells/mL, or $4\times10^5$ cells/mL. In addition, the pH may be pH 6.7 to pH 7.1, or pH 6.8 to pH 7.0. In addition, the dissolved oxygen concentration may be, but is not limited to, 10% to 90%, 20% to 80%, or 30% to 60%.

In a case of producing recombinant proteins through cell culture, in particular animal cell culture, it is common to perform culture at a temperature suitable for cell growth so that productivity increases with extended culture period, and then to perform culture at a temperature lower than the temperature suitable for cell growth so that the cell division cycle is arrested and thus switching to recombinant protein production is achieved (Enhancement of productivity of recombinant α-amidating enzyme by low temperature culture, Furukawa K et al., Cytotechnol, 1999, Vol. 31, 85 to 94; and Enhancing Effect of Low Culture Temperature on Specific Antibody Productivity of Recombinant Chinese Hamster Ovary Cells: Clonal Variation, Yoon S K et al., Biotechnol Prog, 2004, Vol. 20, 1683 to 1688). However, the present inventors have identified that in a case of cell line culture for producing VZV gE antigens, it is advantageous in terms of yield and purity to perform production culture at a temperature lower than a temperature suitable for cell line growth without culture temperature shift, to perform seed culture and/or production culture under a constant temperature condition, or to perform seed culture and production culture under a constant low-temperature condition.

Specifically, the seed culture performing step (a-1) may include culturing the cell line at a temperature of 34° C. to 38° C. In addition, the production culture performing step (a-2) may include culturing the cell line at a temperature of 34° C. to 35.5° C. For example, the cell line may be subjected to seed culture at a temperature of 36° C. to 38° C., 36.5° C. to 37.5° C., or 37° C., and then the cell line that has undergone the seed culture may be subjected to production culture at a temperature of 34° C. to 35.5° C., 34.5° C. to 35.5° C., or 35° C. In addition, the cell line may be subjected to seed culture at a temperature of 34° C. to 35.5° C., 34.5° C. to 35.5° C., or 35° C., and then the cell line that has undergone the seed culture may be subjected to production culture at a temperature of 34° C. to 35.5° C., 34.5° C. to 35.5° C., or 35° C. In addition, the cell line may be subjected to seed culture and production culture at a constant temperature within a temperature range of 34° C. to 35.5° C.

In an embodiment of the present invention, the production culture may be performed by suspension culture. Here, the suspension culture may be carried out at a stirring speed condition of 62 rpm to 72 rpm, 64 rpm to 70 rpm, or 66 rpm to 68 rpm; however, the stirring speed is not limited thereto. The number of cells inoculated in the suspension culture may be, but is not limited to, $2\times10^5$ cells/mL to $5\times10^5$ cells/mL, $3\times10^5$ cells/mL to $4\times10^5$ cells/mL, or $4\times10^5$ cells/mL. The above-mentioned number of cells corresponds to a cell density that is optimal for production culture of VZV gE antigens. In a case where the cell density is less than $2\times10^5$ cells/mL, the amount of protein obtained is small due to a too small number of cells; and in a case where the cell density is greater than $5\times10^5$ cells/mL, a large number of host cell proteins (HCPs), such as cell debris, are also produced, which is problematic in that it is difficult to remove HCPs to a concentration, which meets the pharmaceutical standards, in a purification process. In addition, the pH may be pH 6.7 to pH 7.1, or pH 6.8 to pH 7.0. In addition, the dissolved oxygen concentration may be, but is not limited to, 10% to 90%, 20% to 80%, or 30% to 60%.

In an embodiment of the present invention, the culture may be performed in a flask or bioreactor. However, the present invention is not limited thereto. Types of the flask and bioreactor and the culture conditions may be changed within a range that can be usually adjusted by those skilled in the art. Specifically, a wave bioreactor, a stirred tank bioreactor, and the like may be used which are capable of suspension culture of animal cells; and a culture solution may be subjected to pH adjustment to pH 6.8 to pH 7.2 using $CO_2$ or a base solution, such as sodium carbonate and sodium bicarbonate, and used. However, the present invention is not limited thereto.

For example, the seed culture may be performed by inoculating a cell line into a shake flask and carrying out subculture and suspension culture, to obtain a certain number of cells; and the production culture may be performed by inoculating the cell line, for which a certain number of cells has been obtained, into a bioreactor and carrying out suspension culture, to obtain recombinant proteins.

The culture solution purifying step (b) may comprise steps of: performing anion exchange chromatography; performing hydrophobic interaction chromatography; subjecting the culture solution to treatment with a virus-inactivating agent, to inactivate viruses; performing mixed-mode chromatography; and performing concentration and filtration. The chromatography processes, the virus inactivating process, and the concentration and filtration process may be performed in various sequences to achieve optimal production yield.

In an embodiment of the present invention, the culture solution purifying step (b) may comprise steps of: (b-1) performing anion exchange chromatography; (b-2) performing hydrophobic interaction chromatography; (b-3) subjecting the culture solution to treatment with a virus-inactivating agent, to inactivate viruses, and then performing concentration and diafiltration; (b-4) performing mixed-mode chromatography, to obtain an eluate; and (b-5) subjecting the eluate to concentration and diafiltration, and then performing nanofiltration, the steps being performed in a series of sequences.

In addition, before the culture solution purifying step (b), the culture solution may be subjected to a treatment process for removing cell debris therefrom. For example, a culture filtrate obtained by subjecting the culture solution to filtration may be subjected to the purifying step. Here, the filter medium used for filtration may be a depth filter. In addition, the filter medium may have a pore diameter of 1 μm or smaller, 0.5 μm or smaller, 0.45 μm or smaller, 0.3 μm or smaller, 0.25 μm or smaller, or 0.2 μm or smaller; and a mixture of filter media of various diameters may be used.

As used herein, the term "chromatography" refers to a process of separating a solute of interest, for example, a protein of interest, from other solutes in a mixture under a specific buffering condition, in which the separation is achieved by percolation of the mixture through adsorbents that adsorb or retain solutes more or less strongly due to properties of the solutes, such as pI, hydrophobicity, size, and structure.

In the culture solution purifying step (b), anion exchange chromatography may be used. The anion exchange chromatography can lead to removal of liquid medium compositions and impurities which are contained in a culture solution or a culture filtrate. The anion exchange chromatography may be performed using resins such as DEAE cellulose, POROS™ PI 20, PI 50, HQ 10, HQ 20, HQ 50, D 50 (Applied Biosystems), MONOQ™, MINIQ™, SOURCE™ 15Q and 30Q, Q, DEAE and ANX SEPHAROSE FAST FLOW, Q SEPHAROSE HIGH PERFORMANCE, QAE SEPHADEX™ and Q SEPHAROSE FAST FLOW (GE Healthcare), WP PEI, WP DEAM, WP QUAT (J. T. Baker), HYDROCELL DEAE AND HYDROCELL QA (Biochrom Labs Inc.), UNOSPHERE Q, MACRO-PREP DEAE and MACRO-PREP HIGH Q (Biorad), with Q SEPHAROSE FAST FLOW resin being preferred.

In addition, after equilibration of the column to pH 7.0±0.2, the culture solution to be purified may be loaded at a flow rate of 150±15 cm/hr. Conditions such as type of resin, pH, and flow rate are not limited to those mentioned above, and may be changed within a range that can be usually adjusted by those skilled in the art.

In addition, for the anion exchange chromatography, a wash buffer may be used whose sodium chloride concentration is 150 mM or lower, 0.1 mM to 150 mM, 10 mM to 150 mM, or 100 mM to 150 mM. In addition, an elution buffer may be used whose sodium chloride concentration is 400 mM to 600 mM, 450 mM to 550 mM, or 500 mM. In a case where purification is performed using a wash buffer and an elution buffer, whose sodium chloride concentration is within the above-mentioned range, it is possible to minimize an impurity content in a culture solution containing VZV gE antigens.

In the culture solution purifying step (b), hydrophobic interaction chromatography may be used. The hydrophobic interaction chromatography can be used to remove liquid medium compositions and impurities. The hydrophobic interaction chromatography may be performed using resins such as Butyl FF, Butyl HP, Octyl FF, Phenyl FF, Phenyl HP, Phenyl FF (high sub), Phenyl FF (low sub), Capto Phenyl ImpRes, Capto Phenyl (high sub), Capto Octyl, Capto Butyl ImpRes, Capto Butyl (GE Healthcare), TOYOPEARL® Super Butyl-550C, TOYOPEARL® Hexyl-650C, Butyl-650C, Phenyl-650C, Butyl 600 M, Phenyl-600M, PPG-600M, Butyl-650M, Phenyl-650M, Ether-650M, Butyl-650S, Phenyl-650S, Ether-650S, TSKgel Pheny-SPW, TSKgel Ether-5PW (Tosoh Bioscience), with TOYOPEARL® Butyl-650M (Tosoh Bioscience) being preferred.

In addition, after equilibration of the column to pH 7.0±0.2, the culture solution to be purified, for example, the eluate from the anion exchange chromatography may be loaded at a flow rate of 100±10 cm/hr. Here, before purification, 1 to 10 M, 2 to 8 M, 3 to 7 M, or 5 M of sodium chloride may be added to the solution to be purified. In addition, a wash buffer containing sodium chloride may be used, and an elution buffer containing no sodium chloride may be used. Conditions such as type of resin, pH, and flow rate are not limited to those mentioned above, and may be changed within a range that can be usually adjusted by those skilled in the art.

The culture solution purifying step (b) may comprise a step of subjecting the culture solution to treatment with a virus-inactivating agent, to inactivate viruses. The virus inactivating process can lead to inactivation of potential enveloped viruses in a solution containing VZV gE antigens to be purified.

Specifically, the virus-inactivating agent may be a phosphoric acid solution. For example, the virus-inactivating agent may be added to the eluate from the hydrophobic interaction chromatography so that the pH of the eluate is adjusted to pH 2.8 to pH 3.2, pH 2.9 to pH 3.1, or pH 3.0. In the virus inactivating step, in a case where the pH is less than 2.8, the structure of the VZV gE antigen may be denatured; and in a case where the pH is greater than 3.2, the viruses may not be inactivated.

In the culture solution purifying step (b), mixed-mode chromatography may be performed. The mixed-mode chromatography can lead to removal of dimers and impurities from a solution containing VZV gE antigens. The mixed-mode chromatography may be performed using resins such as BAKERBOND ABX™ (J. T. Baker), Ceramic Hydroxyapatite Types I and II, and Fluoride Hydroxyapatite (Bio-Rad), and MEP and MBI HYPERCEL™ (Pall Corporation), with Ceramic Hydroxyapatite being preferred.

In addition, after equilibration of the column to pH 7.0±0.2, the culture solution to be purified, for example, a solution obtained by performing concentration and filtration on the eluate from the hydrophobic interaction chromatography may be loaded at a flow rate of 100±10 cm/hr. In the mixed-mode chromatography, conditions such as resin, buffer, and pH are not limited to those mentioned above, and may be changed within a range that can be usually adjusted by those skilled in the art.

The culture solution purifying step (b) may comprise a step of performing concentration and filtration. The concentration and filtration process may be performed several times during the purification process of the culture solution, and may be performed between the respective chromatography steps, between the chromatography step and the virus inactivating step, or after the chromatography steps or the virus inactivating step.

For example, before performing the mixed-mode chromatography, concentration and filtration may be performed to obtain a solution having a condition suitable for the mixed-mode chromatography. For example, concentration of VZV gE fractions may be achieved by ultrafiltration and/or diafiltration, and may include one or more tangential flow filtration (TFF) steps.

In addition, after performing the mixed-mode chromatography, concentration and filtration may be performed to adjust the VZV gE antigen concentration. Here, diafiltration may be performed until the pH and conductivity of a filtrate reach desired values, and then ultrafiltration may be used to adjust the protein concentration.

In addition, the culture solution purifying step (b) may comprise a step of performing nanofiltration on the eluate from the mixed-mode chromatography which has been concentrated and filtered. Here, a filtration system with a nanofilter may be used for the nanofiltration. To separate viruses from a solution containing VZV gE antigens, the nanofiltration may be performed using a nanofilter with a pore size of, for example, 75 nm, less than 50 nm, or less than 15 nm.

The culture solution purifying step (b) may further comprise a step of diluting the filtrate obtained by the nanofiltration with a formulation buffer and then performing filtration. Here, the filtration may be performed using a microfilter with a pore size of 0.05 to 0.8 μm, 0.07 to 0.6 μm, or 0.1 to 0.4 μm.

In a case where the filtrate obtained by the nanofiltration during the culture solution purifying step (b), is diluted and filtered using a microfilter, proteins may be obtained in a yield of 97% or higher, 98% or higher, 99% or higher, or 99.5% or higher. In addition, an HCP content in the purified culture solution may be about 180 ppm or lower, 170 ppm or lower, 160 ppm or lower, 150 ppm or lower, 100 ppm or lower, 80 ppm or lower, 70 ppm or lower, 60 ppm or lower, 50 ppm or lower, 30 ppm or lower, or ppm or lower.

MODE FOR THE INVENTION

Hereinafter, the present invention will be described in more detail by way of the following examples. However, the following examples are for illustrative purposes only, and the scope of the present invention is not limited thereto.

Example 1. Construction of Expression Vector for Varicella Zoster Virus Surface Protein Antigen and Transformation The Varicella Zoster Virus (VZV) surface protein (gE) antigen variant gene (MGgE; SEQ ID NO: 2) disclosed in International Publication No. WO 2019/225962 A1 was cloned into the pMSID2 vector disclosed in Korean Patent No. 1591823, to construct the pMSID2-MGgE expression vector (FIG. 2). Next, the expression vector was transfected into CHO DG44 (Thermo Fisher Scientific, USA) host cells, which had been adapted to a chemically defined medium (CDM4CHO (+0/20 nM MTX; methotrexate)), to produce a cell line (MGgE-CHO DG44) that highly expresses the Varicella Zoster Virus surface protein antigen (MGgE; SEQ ID NO: 1).

Example 1.1. Identification of Protein Productivity Depending on Antigen and Cell Line To identify the protein productivity depending on types of antigen and cell line, the pMSID2-MGgE expression vector constructed in Example 1 and the pMSID2-GSKgE expression vector constructed by cloning, into the pMSID2 vector, a gene encoding the truncated gE antigen (GSKgE; SEQ ID NO: 4) disclosed in Korean Patent No. 1357204 were respectively transfected into CHO-S host cells, which had been adapted to a chemically defined medium (CD forti CHO (+50 nM MTX)), to produce cell lines (MGgE-CHO-S and GSKgE-CHO-S).

The MGgE-CHO DG44, MGgE-CHO-S, and GSKgE-CHO-S were respectively cultured in the chemically defined medium for 6 days, and then the expression level of VGV gE was checked by Western blotting and enzyme-linked immunosorbent assay (ELISA).

As a result, referring to FIGS. 3 and 4, MGgE showed better productivity than GSKgE in the CHO-S cell line, and MGgE showed much better productivity in the CHO DG44 cell line than in the CHO-S cell lines. In particular, MGgE showed the highest productivity in the CHO DG44(S) cell line that had been adapted to CDM4CHO (+20 nM MTX) medium.

Example 2. Establishment of Culture Method for MGgE Production

Example 2.1. Seed Culture to Obtain Certain Number of Cells for Cell Line

The MGgE-CHO DG44 cell line produced in Example 1 was inoculated into a 500 mL flask to a total of 100 mL at $3\times10^5$ cells/mL or higher, and cultured under a condition at 36° C. to 38° C. and 4% to 6% $CO_2$. Then, a step of inoculating the cell line at $2\times10^5$ cells/mL to $5\times10^5$ cells/mL to a total of 200 mL to 800 mL at intervals of 2 to 4 days was repeated while increasing a flask volume, to obtain a certain number of cells. The cells obtained in the flask were inoculated into a bioreactor at a concentration of $2\times10^5$ cells/mL to $5\times10^5$ cells/mL, and then suspension culture was carried out under a condition at 36° C. to 38° C., pH 6.7 to pH 7.1, 10% to 90% dissolved oxygen, and a stirring speed of 86 rpm to 96 rpm. In this manner, a certain number of cells was obtained.

Example 2.2. Production Culture of MGgE Antigen

The MGgE-CHO DG44 cell line, for which a certain number of cells had been obtained in Example 2.1, was inoculated into a bioreactor at a cell concentration of $2\times10^5$ cells/mL to $5\times10^5$ cells/mL, and then suspension culture was carried out under a condition at a temperature of 34° C. to 35.5° C., pH 6.7 to pH 7.1, 10% to 90% dissolved oxygen, and a stirring speed of 62 rpm to 72 rpm.

Example 2.3. Quantification of MGgE Antigen

In the following examples, ELISA was performed to measure a content of the MGgE antigen. Specifically, the VZV gE antibody (Cat. #sc-17549, 200 μg/mL) was diluted in PBS to a concentration of 1 μg/mL, and then the resultant was added to a 96-well ELISA plate at 100 μL per well. Overnight incubation (coating) was performed at 4° C. The plate was washed 3 times with a washing solution (0.05% Tween 20/phosphate-buffered saline (PBS)), and then incubated for 1 hour with a PBS solution containing 2% BSA. The ELISA plate was washed again, and then incubated for 2 hours with addition of diluted samples. Then, the plate was washed again. Each of culture solution samples was centrifuged, and then the supernatant was stored at −20° C. or lower. The sample was thawed at room temperature 1 hour before measurement and used. The VZV gE antibody (Cat. #sc-56995, 100 μg/mL) was diluted to a concentration of 1 μg/mL, added at 100 μL per well, and incubated at room temperature for 1 hour. The plate was washed. Then, goat anti-mouse IgG-HRP was diluted to a concentration of 1/1000, and then added thereto at 100 μL per well. The plate was incubated at room temperature for 1 hour. The plate was washed, and 3,3,5,5'-tetramethyl benzidine (TMB) was added thereto to induce HRP reaction. Then, 100 μL of 1 N $H_2SO_4$ per well was dispensed thereto to stop the reaction, and the absorbance was measured at 450 nm with a microplate reader. A content of the sample was calculated by substituting the measured absorbance into the standard curve equation and multiplying the resulting value by a dilution factor.

Experimental Example 1. Identification of Productivity Following Culture Temperature Shift To identify an effect of culture temperature shift on the productivity of the MGgE antigen at the time when it is determined that the cells have been sufficiently grown during the production culture step, the MGgE-CHO DG44 cell line, for which a certain number of cells was obtained, in Example 2.1 was inoculated into a bioreactor at a cell concentration of 2×10$^5$ cells/mL to 5×10$^5$ cells/mL and subjected to suspension culture. Then, when the cell line reached a cell concentration of about 60×10$^5$ cells/mL, 80×10$^5$ cells/mL, and 150×10$^5$ cells/mL, respectively, the culture temperature was lowered to 32° C. and production culture was carried out. In addition, the MGgE-CHO DG44 cell line, for which a certain number of cells was obtained, in Example 2.1 was subjected to production culture under a constant temperature condition of 37° C., and then the MGgE antigen productivity was compared (see Table 1, FIGS. 5A and 5B).

TABLE 1

| Process parameter | w/o temp. shift | Temp. shift (37→32° C.) (1) | (2) | (3) |
|---|---|---|---|---|
| Temperature (° C.) | 37.0 ± 0.5 | 37.0 ± 0.5 → 32.0 ± 0.5 | | |
| Temperature shift point (×10$^5$ cells/mL) | N/A | Approximately 60 | Approximately 80 | Approximately 150 |
| Culture duration (day) | 11.5 | 14 | 14 | 14 |
| Harvest productivity (mg/L) | 1576 ± 28 | 1096 | 1248 | 1183 ± 115 |
| $q_P$ (pg/cell/day) | 13.7 ± 0.7 | 11.9 | 11.5 | 7.7 ± 0.5 |

As a result, referring to Table 1 and FIGS. 5A and 5B, it can be seen that in a case where the temperature shift occurred, a culture duration during which the cell line survives increased, whereas the MGgE antigen productivity ($q_P$) was rather lower than a case of the constant temperature condition.

This suggests that during production culture of the MGgE antigen, in a case where the culture temperature for the MGgE-CHO DG44 cell line is maintained within a certain range without temperature shift, the productivity is improved.

Experimental Example 2. Identification of MGgE Antigen Productivity Depending on Production Temperature In the production culture step of the MGgE antigen in Example 2.2, the MGgE-CHO DG44 cell line, which was inoculated into a bioreactor at a cell concentration of 2×10$^5$ cells/mL to 5×10$^5$ cells/mL, was subjected to production culture under a constant temperature condition selected within a range of 33° C. to 37° C. (Table 2, FIGS. 6A and 6B).

TABLE 2

| Process | Process parameter 33.0° C. | 33.5° C. | 34.0° C. | 34.5° C. | 35.0° C. | 35.5° C. | 37.0° C. |
|---|---|---|---|---|---|---|---|
| performance | Temperature 33.0° C. | 33.5° C. | 34.0° C. | 34.5° C. | 35.0° C. | 35.5° C. | 37.0° C. |
| Integral VCD (×10$^5$ cells/mL · day) | 121.4 | 645.7 | 1681.4 | 1848.1 | 1705.7 | 1312.2 | 849.6 |
| Culture duration (day) | 11 | 16 | 14 | 14 | 14 | 12 | 10 |
| Harvest productivity (mg/L) | 205 | 880 | 2711 | 3268 | 3247 | 2196 | 1142 |
| $q_P$ (pg/cell/day) | 16.9 | 13.6 | 16.1 | 17.7 | 19.0 | 16.7 | 13.4 |

As a result, referring to Table 2, and FIGS. 6A and 6B, the culture duration and the productivity increased under a low-temperature culture condition (a constant temperature condition of 34° C. to 35.5° C.) lower than 37° C. that is a suitable temperature for common CHO cells to grow. In addition, under a condition of 33.5° C. or lower, the cell growth and the productivity decreased. On the other hand, from the viewpoint that $q_P$ is related to the number of cells in culture, the reason why the value of $q_P$ was calculated to be rather high at 33° C. is that despite poor productivity, the number of cells is very small as compared with other batches (see the integral VCD value). That is, it can be seen that the low-temperature condition of 34° C. to 35.5° C. resulted in remarkably improved MGgE antigen productivity in the MGgE-CHO DG44 cell line.

Example 3. Purification of MGgE Antigen

Example 3.1. Harvest and Clarification

For the culture solution (MG1120) cultured at 35° C. that was a condition for the production culture in Experimental Example 2, to remove cell debris in the culture solution, a depth filter (COHC Millipore, USA) was used to perform harvest and clarification.

A pressure condition during filtration was maintained at 0.9 bar or lower, and the filtrate obtained by removing cell debris was filtered with a 0.45+0.2 μm filter (SARTOPORE II, Sartorius, Germany) to obtain a culture filtrate.

Example 3.2. Anion Exchange Chromatography—Comparison of Yields Depending on Sodium Chloride Concentration in Wash Buffer and Elution Buffer Anion exchange chromatography was performed to remove liquid medium compositions and impurities contained in the culture filtrate obtained in Example 3.1.

Specifically, the column was filled with Q SEPHAROSE FF (GE Healthcare, USA) resin, and then equilibrated to a pH of 7.0±0.2 using an equilibration buffer. Then, the culture filtrate obtained in Example 3.1. was loaded onto the column so that the flow rate was 150±15 cm/hr. Subsequently, the column was washed sequentially with the equilibration buffer and a wash buffer containing sodium chloride. Then, the MGgE antigen was eluted using an elution buffer containing sodium chloride, and collected.

In cases where the concentration of sodium chloride contained in the wash buffer and the elution buffer was changed, the yields in the anion exchange chromatography step were compared.

Specifically, anion exchange chromatography was performed using a wash buffer containing 150 mM, 200 mM, or 250 mM sodium chloride and an elution buffer containing 500 mM sodium chloride (Table 3).

TABLE 3

| Wash buffer condition | | gE total (ug) | | | HCP total (ug) | | | Eluate | | |
|---|---|---|---|---|---|---|---|---|---|---|
| pH | NaCl conc. (mM) | Loading solution | Eluate | Yield (%) | Loading solution | Eluate | Yield (%) | MGgE total (ug) | HCP total (ug) | HCP/MGgE (%) |
| 7 | 150 | 253601 | 163781 | 64.6 | 171929 | 5401 | 3.1 | 163781 | 5400.8 | 3.3 |
| | 200 | 253601 | 87608 | 34.5 | 171929 | 3082 | 1.8 | 87608 | 3081.6 | 3.5 |
| | 250 | 200780 | 29096 | 14.5 | 231663 | 1802 | 0.8 | 29096 | 1802.4 | 6.2 |

As a result, referring to Table 3, in a case where the concentration of sodium chloride in the wash buffer was 150 mM, a content of impurities per MGgE was the lowest.

Accordingly, anion exchange chromatography was performed using a wash buffer containing 150 mM sodium chloride and an elution buffer containing 400 mM, 500 mM, or 600 mM sodium chloride (Table 4).

TABLE 4

| Elution buffer condtition | | gE total (ug) | | | HCP total (ug) | | | Eluate | | |
|---|---|---|---|---|---|---|---|---|---|---|
| pH | NaCl conc. (mM) | Loading solution | Eluate | Yield (%) | Loading solution | Eluate | Yield (%) | MGgE total (ug) | HCP total (ug) | HCP/MGgE (%) |
| 7 | 400 | 253601 | 81152 | 32.0 | 171929 | 3093 | 1.8 | 81152 | 3093 | 3.8 |
| | 500 | 253601 | 87608 | 34.5 | 171929 | 3082 | 1.8 | 87608 | 3082 | 3.5 |
| | 600 | 200780 | 86710.4 | 43.2 | 231663 | 3669 | 1.6 | 86710 | 3669 | 4.2 |

As a result, referring to Table 4, in a case where an elution buffer containing 500 mM sodium chloride was used, a content of impurities per MGgE was the lowest.

Therefore, the optimal concentrations of sodium chloride contained in the wash buffer and the elution buffer in the anion exchange chromatography during the purification step of the MGgE antigen are 150 mM and 500 mM, respectively.

Example 3.3. Hydrophobic Interaction Chromatography

Hydrophobic interaction chromatography was performed on the eluate from the anion exchange chromatography, which was obtained in Example 3.2, to remove liquid medium compositions and impurities which were not previously removed.

Specifically, the column was filled with Toyopearl Butyl-650M (Tosoh) resin, and then equilibrated to a pH of 7.0±0.2 using an equilibration buffer. Then, 5 M sodium chloride was added to the eluate from the anion exchange chromatography eluate, which was obtained in Example 3.2, and the resultant was loaded onto the column so that the flow rate was 100±10 cm/hr. Subsequently, the column was washed sequentially with the equilibration buffer and a wash buffer containing 1 M sodium chloride. Then, the MGgE antigen was eluted using an elution buffer containing no sodium chloride, and collected.

Example 3.4. Virus Inactivation

To inactivate potential enveloped viruses in the solution containing the MGgE antigen, a virus inactivating step was performed with addition of a solvent.

Specifically, phosphoric acid was added to the eluate from the hydrophobic interaction chromatography, which was obtained in Example 3.3, so that the pH of the eluate was adjusted to 3.0±0.2, and stirring was performed at 100±20 rpm for 30 minutes (control) at room temperature, to inactivate viruses. Then, disodium phosphate was used to adjust the pH to 6.5±0.5.

In addition, the stability of the MGgE antigen was checked while changing the virus inactivation time to 60 minutes, 90 minutes, and 120 minutes (Table 5).

TABLE 5

| pH | Inactivation time (min) | Content (μg/mL) UV content | gE ELISA | Purity (%) SE-HPLC |
|---|---|---|---|---|
| 3.0 | 30 (control) | 598 | 776 | 93.61 |
| | 60 | 593 | 827 | 93.13 |
| | 90 | 585 | 760 | 92.80 |
| | 120 | 571 | 795 | 93.48 |
| | % after 120-min reaction relative to initial value | 95% | 103% | 100% |

As a result, referring to Table 5, even the 120 minute-inactivation did not cause significant changes in content and purity of the MGgE antigen. Therefore, under a pH 3.0 condition effective for virus inactivation, MGgE was stable even in a case where the virus inactivation time was 120 minutes.

Example 3.5. 1st Concentration and Diafiltration

A 1st concentration and diafiltration step was performed so that low molecular ions were removed from the solvent-added MGgE antigen-containing solution obtained in Example 3.4 and the solution had a condition suitable for a mixed-mode chromatography process.

Specifically, the solvent-added MGgE antigen-containing solution was subjected to ultrafiltration using an ultrafiltration/diafiltration system (Sartocon Cassette (50K)), and the filtrate was subjected to diafiltration using an equilibration buffer for the mixed-mode chromatography process, which is the next process, until the filtrate had a pH of 7.2±0.2 and a conductivity of 2.5 mS/cm or lower.

Example 3.6. Mixed-Mode Chromatography

Mixed-mode chromatography was performed on the MGgE antigen-containing solution having undergone dialysis and/or concentration, which was obtained in Example 3.5, to remove dimers and impurities therefrom.

Specifically, the column was filled with Ceramic Hydroxyapatite (Bio-Rad) resin, and then equilibrated to a pH of 7.2±0.2 using an equilibration buffer. Then, the MGgE antigen-containing solution having undergone dialysis and/or concentration, which was obtained in Example 3.5, was loaded onto the column so that the flow rate was 100±10 cm/hr, with the non-adsorbed solution being collected. Then, the column was washed with an equilibration buffer for collection.

Example 3.7. 2nd Concentration and Diafiltration

A 2nd concentration and diafiltration step was performed so that the protein concentration in the non-adsorbed solution from the mixed-mode chromatography, which was obtained in Example 3.6, was adjusted and the solution had a condition suitable for a nanofiltration process.

The non-adsorbed solution from the mixed-mode chromatography was subjected to an ultrafiltration/diafiltration system (SARTOCON™ Cassette (50K)), and the filtrate was subjected to diafiltration using an equilibration buffer for the nanofiltration process, which is the next process, until the filtrate had a pH of 7.4±0.2 and a conductivity of 15.5 mS/cm or higher. Then, the resultant was concentrated by ultrafiltration to a protein concentration of 7.0±0.5 mg/mL.

Example 3.8. Nanofiltration

Nanofiltration is a virus removal step, in which a nanofilter (PLANOVA™ 20N, Asahi) was used and a formulation buffer was used to equilibrate the pH to 7.4±0.2.

Then, the MGgE antigen-containing solution having undergone dialysis and concentration, which was obtained in Example 3.7, was passed through the nanofilter under a pressure condition of 1.0±0.2 bar to remove viruses, and then the nanofilter was washed with the equilibration buffer. The filtrate obtained by nanofiltration and the washing solution were mixed together, and then the protein concentration was measured.

Example 3.9. Dilution and Filtration

The filtrate obtained by nanofiltration in Example 3.8 was diluted with a formulation buffer so that the protein concentration was 5.0±0.5 mg/mL, and then filtration was performed using a 0.2 inn filter.

Then, the obtained MGgE antigen-containing solution was aliquoted and stored at −20° C. or lower.

Experimental Example 3. Yield Evaluation for Each Purification Step

The yield for each step in the purification step was checked by measuring a content of the MGgE antigen for each step in Example 3 (Table 6). With respect to the protein content for MGgE in Table 6, each culture solution, marked with *, which underwent the harvest and clarification and the anion exchange chromatography steps, was measured with an ELISA test; and the culture solution in subsequent steps was measured with UV.

TABLE 6

| Process | MGgE Protein content (g) | Yield (%) | HCP ppm | LRV | SE-HPLC % |
|---|---|---|---|---|---|
| Harvest and | 334.0 * | — | — | — | — |
| clarification | 254.5 * | 76% | — | — | — |
| Anion exchange | 251.0 * | — | 199488.8 | — | — |
| chromatography | 199.8 * | 80% | 13854.9 | 1.16 | 85.48 |
| Hydrophobic | 231.3 | — | 10914.2 | — | — |
| interaction chromatography | 126.9 | 55% | 4432.8 | 0.39 | 91.86 |
| Virus inactivation | 125.5 | — | 4432.8 | — | — |
| | 125.1 | 100% | 3335.2 | 0.12 | 99.21 |
| 1st concentration | 124.6 | — | 3335.2 | — | — |
| and diafiltration | 105.0 | 84% | 3258.0 | 0.01 | 95.24 |
| Mixed-mode | 104.1 | — | 3258.0 | — | — |
| chromatography | 107.3 | 103% | 423.6 | 0.89 | 97.43 |
| 2nd concentration | 106.8 | — | 423.6 | — | — |
| and diafiltration | 108.0 | 101% | 216.3 | 0.29 | 99.26 |
| Nanofiltration | 101.0 | — | 216.3 | — | — |
| | 91.5 | 91% | 197.3 | 0.04 | 99.27 |
| Dilution and | 89.4 | — | — | — | — |
| filtration | 100.5 | — | — | — | 99.32 |
| Drug substance | 100.5 | — | 180.4 | — | — |
| (antigen) | 97.5 | 97% | 172.6 | 0.02 | 99.32 |

The invention claimed is:

1. A method for producing Varicella Zoster Virus (VZV) surface protein (gE) antigens, comprising steps of:

(a) culturing a recombinant cell line prepared using Chinese hamster ovary (CHO) cell that produces the VZV gE antigens, to obtain a culture solution; and (b) purifying the culture solution, wherein the culturing step (a) comprises steps of:

(a-1) performing seed culture on the recombinant cell line; and (a-2) performing production culture on the cell line that has undergone the seed culture, wherein the step (a-2) comprises culturing the cell line at a temperature of 34° C. to 35.5° C., and wherein the purifying step (b) comprises steps of:

(b-1) performing anion exchange chromatography;

(b-2) performing hydrophobic interaction chromatography, comprising adding sodium chloride to an eluate obtained through the anion exchange chromatography and loading it onto a hydrophobic interaction chromatography column, and washing with a washing buffer containing sodium chloride;

(b-3) subjecting the culture solution to treatment with a virus-inactivating agent, to inactivate viruses, and then performing concentration and diafiltration;

(b-4) performing mixed-mode chromatography, to obtain an eluate; and (b-5) subjecting the eluate to concentration and diafiltration, and then performing nanofiltration, the steps being performed in a series of sequences.

2. The method of claim 1, wherein the VZV gE antigen is a polypeptide consisting of the amino acid sequence of SEQ ID NO: 1.

3. The method of claim 1, wherein the cell line is transformed with a gene consisting of the nucleotide sequence of SEQ ID NO: 2.

4. The method of claim 1, wherein the seed culture performing step (a-1) is such that the recombinant cell line is cultured by any one method selected from the group consisting of subculture, suspension culture, and combinations thereof.

5. The method of claim 1, wherein the seed culture performing step (a-1) includes culturing the recombinant cell line at a temperature of 34° C. to 38° C.

6. The method of claim 1, wherein for the anion exchange chromatography, a wash buffer is used whose sodium chloride concentration is 0.1 mM to 150 mM.

7. The method of claim 1, wherein for the anion exchange chromatography, an elution buffer is used whose sodium chloride concentration is 400 mM to 600 mM.

8. The method of claim 1, wherein the virus-inactivating agent is a phosphoric acid solution.

9. The method of claim 1, wherein the virus inactivating step is performed under a condition of pH 2.8 to 3.2.

10. The method of claim 1, wherein for the nanofiltration step (b-5), a filtration system with a nanofilter is used.

11. The method of claim 1, further comprising:

after the step (b-5), a step of diluting the filtrate obtained by the nanofiltration with a formulation buffer, and then performing filtration.

12. The method of claim 1, wherein for the anion exchange chromatography, a wash buffer is used whose sodium chloride concentration is 0.1 mM to 150 mM.

13. The method of claim 1, wherein for the anion exchange chromatography, an elution buffer is used whose sodium chloride concentration is 400 mM to 600 mM.

14. The method of claim 1, wherein the virus-inactivating agent is a phosphoric acid solution.

15. The method of claim 1, wherein the virus inactivating step is performed under a condition of pH 2.8 to 3.2.

* * * * *